(12) United States Patent
Iga et al.

(10) Patent No.: US 11,920,123 B2
(45) Date of Patent: Mar. 5, 2024

(54) CELL ANALYZING DEVICE AND CELL ANALYZING SYSTEM

(71) Applicant: EVIDENT CORPORATION, Nagano (JP)

(72) Inventors: Yasunobu Iga, Tachikawa (JP); Taiji Mine, Machida (JP); Yoshinobu Akahori, Hachioji (JP)

(73) Assignee: Evident Corporation, Nagano (JP)

( * ) Notice: Subject to any disclaimer, the term of this patent is extended or adjusted under 35 U.S.C. 154(b) by 308 days.

(21) Appl. No.: 16/929,228

(22) Filed: Jul. 15, 2020

(65) Prior Publication Data

US 2020/0339939 A1 Oct. 29, 2020

Related U.S. Application Data

(63) Continuation of application No. PCT/JP2018/000797, filed on Jan. 15, 2018.

(51) Int. Cl.
*C12M 1/34* (2006.01)
*G02B 21/06* (2006.01)
*G02B 21/36* (2006.01)
*G06T 7/00* (2017.01)

(52) U.S. Cl.
CPC .......... *C12M 41/36* (2013.01); *G02B 21/06* (2013.01); *G02B 21/365* (2013.01); *G06T 7/0012* (2013.01); *G06T 2207/30024* (2013.01)

(58) Field of Classification Search
None
See application file for complete search history.

(56) References Cited

U.S. PATENT DOCUMENTS

| 8,101,553 | B1* | 1/2012 | Kurosawa | C07K 16/00 |
| | | | | 506/26 |
| 8,447,092 | B2 | 5/2013 | Kii et al. | |
| 8,824,767 | B2 | 9/2014 | Takagi et al. | |
| 10,416,433 | B2 | 9/2019 | Matsumoto | |
| 10,656,136 | B2 | 5/2020 | Kiyota et al. | |
| 10,872,411 | B2* | 12/2020 | Hattori | G06V 20/698 |
| 11,068,695 | B2* | 7/2021 | Kii | G06T 7/0016 |

(Continued)

FOREIGN PATENT DOCUMENTS

| JP | 2006271210 A | 10/2006 |
| JP | 2007306889 A | 11/2007 |

(Continued)

OTHER PUBLICATIONS

Japanese Office Action (and English language translation thereof) dated Jul. 20, 2021 issued in counterpart Japanese Application No. 2019-564263.

(Continued)

*Primary Examiner* — Nancy Bitar
(74) *Attorney, Agent, or Firm* — Holtz, Holtz & Volek PC (57) ABSTRACT

A cell analyzing device includes a control circuit. The control circuit acquires data of an observation image. The control circuit specifies a colony of a cultured cell in the observation image. The control circuit calculates a ratio at which the cultured cell occupies a predetermined range included in the observation image as an occupancy rate. The control circuit calculates a size of the colony. The control circuit determines a state of the cultured cell based on the occupancy rate and the size of the colony.

9 Claims, 8 Drawing Sheets

(56) References Cited

U.S. PATENT DOCUMENTS

| | | | | |
|---|---|---|---|---|
| 2015/0133185 A1* | 5/2015 | Chen | ............... | H04W 72/1215 |
| | | | | 455/552.1 |
| 2015/0193951 A1* | 7/2015 | Lee | ................ | G06F 3/04883 |
| | | | | 345/593 |
| 2016/0370569 A1* | 12/2016 | Matsumoto | ........ | G01N 15/1475 |
| 2017/0073630 A1* | 3/2017 | Matsubara | ........... | G06V 20/693 |
| 2017/0191021 A1 | 7/2017 | Wakui | | |
| 2017/0199171 A1* | 7/2017 | Kiyota | ................ | G06V 20/698 |
| 2018/0032787 A1* | 2/2018 | Iga | ....................... | G06T 7/0002 |
| 2018/0112173 A1* | 4/2018 | Wiles | ...................... | C12Q 1/02 |

FOREIGN PATENT DOCUMENTS

| | | |
|---|---|---|
| JP | 2011024485 A | 2/2011 |
| JP | 2014014352 A | 1/2014 |
| JP | 2014217353 A | 11/2014 |
| JP | 2016059329 A | 4/2016 |
| WO | 2015133185 A1 | 9/2015 |
| WO | 2015193951 A1 | 12/2015 |

OTHER PUBLICATIONS

English Language translation of an International Preliminary Report on Patentability (IPRP) dated Jul. 21, 2020 issued in International Application No. PCT/JP2018/000797.

International Search Report (ISR) (and English language translation thereof) dated Apr. 17, 2018 issued in International Application No. PCT/JP2018/000797.

* cited by examiner

CELL ANALYZING DEVICE AND CELL ANALYZING SYSTEM

CROSS-REFERENCE TO RELATED APPLICATIONS

This application is a Continuation Application of PCT Application No. PCT/JP2018/000797, filed Jan. 15, 2018, the entire contents of which are incorporated herein by reference.

FIELD

The embodiments relate generally to a cell analyzing device and a cell analyzing system.

BACKGROUND

In cell culture or various applications using cultured cells, it is important to determine the state of the cultured cells. There may be a variety of factors for determining the state of a cell. For example, International Publication No. WO 2015/193951 discloses specifying a colony region based on an image of cultured cells and calculating the area of the colony region, which is an indicator representing the size of the colony. In addition, for example, Jpn. Pat. Appln. KOKAI Publication No. 2007-306889 discloses that the confluency of cells in a culture vessel is calculated from an image.

SUMMARY

A cell analyzing device according to an aspect includes a control circuit. The control circuit acquires data of an observation image. The control circuit specifies a colony of a cultured cell in the observation image. The control circuit calculates a ratio at which the cultured cell occupies a predetermined range included in the observation image as an occupancy rate. The control circuit calculates a size of the colony. The control circuit determines a state of the cultured cell based on the occupancy rate and the size of the colony.

Advantages of the embodiments will be set forth in the description which follows, and in part will be obvious from the description, or may be learned by practicing the invention. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

DETAILED DESCRIPTION

First Embodiment

[Outline of Cell Analyzing System]

The present embodiment relates to a cell analyzing device and a cell analyzing system. In cell culture or various applications using cultured cells, information on the state of cells in culture is valuable information. The cell analyzing system according to the present embodiment acquires an image of a cultured cell and acquires information relating to the state of the cultured cell based on the image.

[Configuration of Cell Analyzing System]

Figure 1:
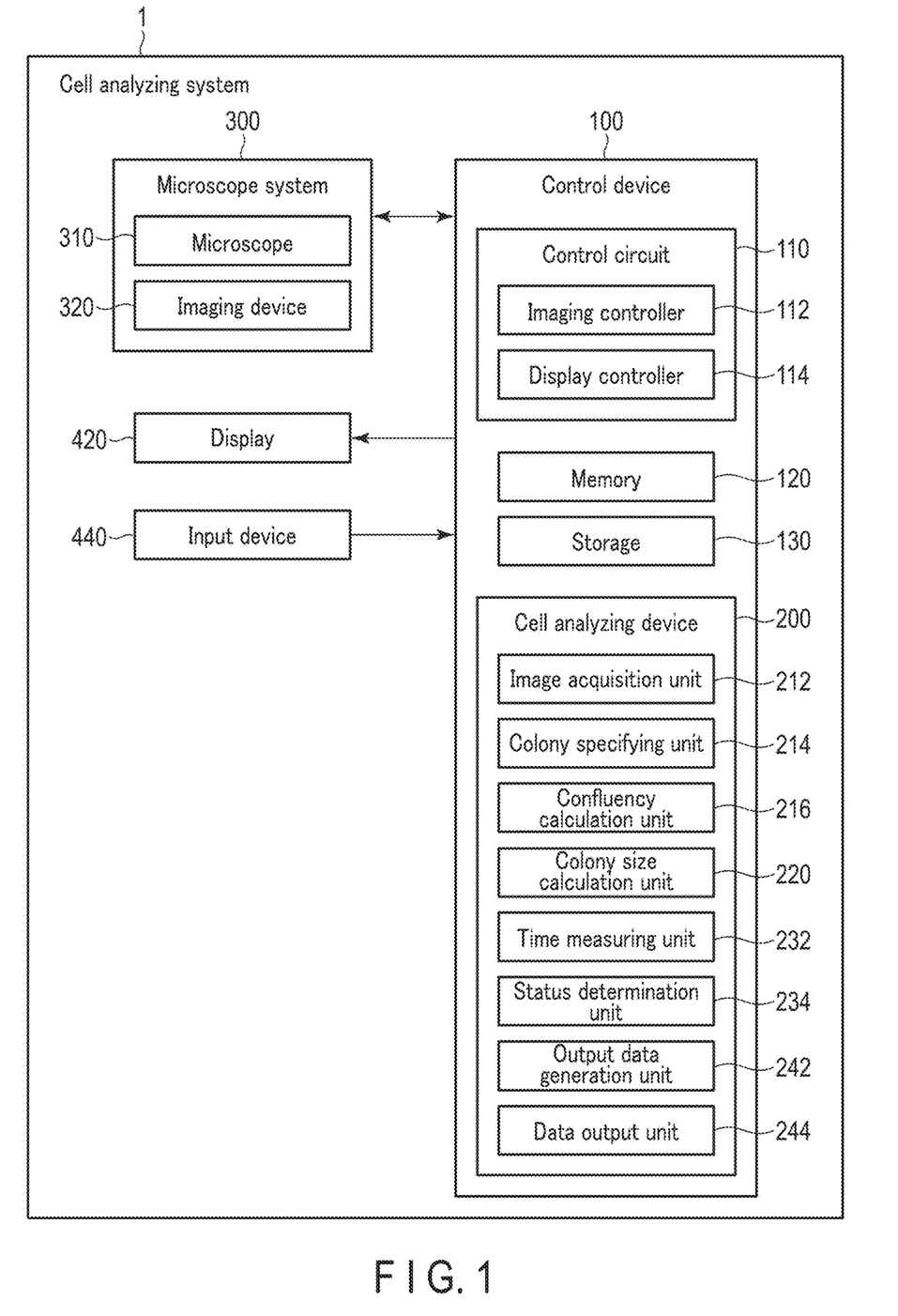
FIG. 1 is a block diagram schematically showing a configuration example of a cell analyzing system according to a first embodiment.

An embodiment of the present invention will be explained with reference to the drawings. FIG. 1 schematically shows a configuration example of a cell analyzing system 1 according to the present embodiment. As shown in FIG. 1, the cell analyzing system 1 includes a microscope system 300 that performs magnified observation of cultured cells and acquires images thereof. The microscope system 300 includes a microscope 310 and an imaging device 320. The microscope 310 can be any microscope suitable for observing cultured cells, such as an optical microscope. The imaging device 320 is, for example, a microscope camera for capturing an image magnified by a microscope. The imaging device 320 is attached to a camera port or the like of the microscope 310 and is configured to generate an observation image related to a microscope image by imaging. In the cell analyzing system 1, the microscope system 300 may be any type of device as long as it can acquire an image of cultured cells. For example, in the case of periodically acquiring an image of cells in culture, an imaging device or the like combined with the culture device may be used.

The cell analyzing system 1 includes a control device 100, a display 420, and an input device 440. The control device 100 may be configured by a computer such as a personal computer. As the display 420, various displays such as a liquid crystal display and an organic EL display can be used. The input device 440 may include various input devices such as a keyboard, a mouse, and a touch panel.

The control device 100 includes an integrated circuit for calculation such as a central processing unit (CPU). In addition, the control device 100 includes a memory 120 including a read only memory (ROM) in which a BIOS or the like is recorded, a random access memory (RAM) such as a dynamic RAM (DRAM) or a static RAM (SRAM) operating as a main storage device of the CPU, and the like. In addition, the control device 100 includes a storage 130 that records various kinds of information such as programs and parameters used in the CPU, image data of cells, data of analysis results, and the like. For example, a hard disk drive (HDD) or a solid state drive (SSD) may be used as the storage 130.

The control device 100 operates as a control unit that controls the operation of the cell analyzing system 1. For example, the CPU of the control device 100 operates as a control circuit 110. The control circuit 110 performs various calculations and outputs an operation command to each unit. The control device 100 can receive a user's instruction from the input device 440 and perform various operations based on the instruction. The control circuit 110 operates as an imaging controller 112, a display controller 114, and the like. The imaging controller 112, for example, controls the operation of the imaging device 320 of the microscope system 300 and, for example, causes the imaging device 320 to acquire an image of cultured cells. The control device 100 acquires an image obtained by the imaging device 320 from the imaging device 320. Furthermore, in the case where the microscope 310 is an electric microscope, the control circuit 110 may control the operation of the microscope 310. The display controller 114 causes the display 420 to display various kinds of information such as an image obtained by the imaging device 320, an analysis result obtained based on the image, and a state of the cell analyzing system 1.

The control device 100 operates as a cell analyzing device 200. The cell analyzing device 200 may be realized by, for example, the CPU of the control device 100, or may be realized by an integrated circuit such as an application specific integrated circuit (ASIC), a field programmable gate array (FPGA), or a graphics processing unit (GPU) provided in the control device 100 instead of the CPU. The cell analyzing device 200 may be configured by one integrated circuit or the like, or may be configured by combining a plurality of integrated circuits or the like. The operation of the cell analyzing device 200 is performed according to, for example, a program recorded in the storage 130 or a recording area of the integrated circuit.

The cell analyzing device 200 operates as an image acquisition unit 212, a colony specifying unit 214, a confluency calculation unit 216, a colony size calculation unit 220, a time measuring unit 232, a status determination unit 234, an output data generation unit 242, and a data output unit 244.

The image acquisition unit 212 acquires, for example, data of an observation image in which cultured cells are captured, which is obtained using the imaging device 320. The colony specifying unit 214 specifies a colony region indicating a colony included in the image with respect to the analysis target region in the acquired image, and specifies a contour of the colony, a region inside the colony, a region outside the colony, and the like.

The confluency calculation unit 216 calculates the ratio of cells in the range of the image to be analyzed as the occupancy rate (confluency). The colony size calculation unit 220 calculates information on the size of the specified colony. The time measuring unit 232 measures an elapsed time from a reference time point, such as a time from the start of culture.

The status determination unit 234 determines the state of the cell in the image based on the acquired various kinds of information. The output data generation unit 242 generates output data as an output of the cell analyzing device 200. For example, the output data generation unit 242 generates output data including the confluency calculated by the confluency calculation unit 216, information on the size of the colony calculated by the colony size calculation unit 220, information on the elapsed time measured by the time measuring unit 232, the determination result of the status determination unit 234, and the like. The data output unit 244 outputs the output data generated by the output data generation unit 242. The output data may be recorded in, for example, the storage 130. An image based on the output data may be displayed on the display 420.

[Operation of Cell Analysis System]

The cell analyzing system 1 captures an image of the cultured cells using the microscope system 300, for example, periodically or at a timing instructed by the user, and acquires an observation image of the cultured cells. That is, the control device 100 causes the imaging device 320 to capture an image related to the microscopic image of the cultured cells magnified by the microscope 310 based on, for example, an operation of the user. The control device 100 stores the observation image obtained by the imaging in the storage 130. For example, every time a new observation image is obtained, the cell analyzing device 200 of the control device 100 analyzes the observation image obtained by imaging. The cell analyzing device 200 determines the state of a cell. The control device 100 causes the display 420 to appropriately display an observation image obtained by imaging, an analysis result obtained by the cell analyzing device 200, or the like, or causes the storage 130 to store the observation image, the analysis result, or the like.

An example of the state of the cell indicated by the cell analyzing device 200 is to specify a cell at an appropriate timing to start differentiation induction. For example, in the case of culturing stem cells such as iPS cells or ES cells, it is known that the timing of starting differentiation induction is important in differentiating these stem cells into specific cells. The cell analyzing device 200 outputs a timing at which differentiation induction should be started based on, for example, the confluency of cells and the size of colonies. In order to determine the timing at which differentiation induction should be started, it is preferable to further consider the culture time, that is, for example, the elapsed time from the start of culture.

[Operation of Cell Analyzing Device]

Figure 2:
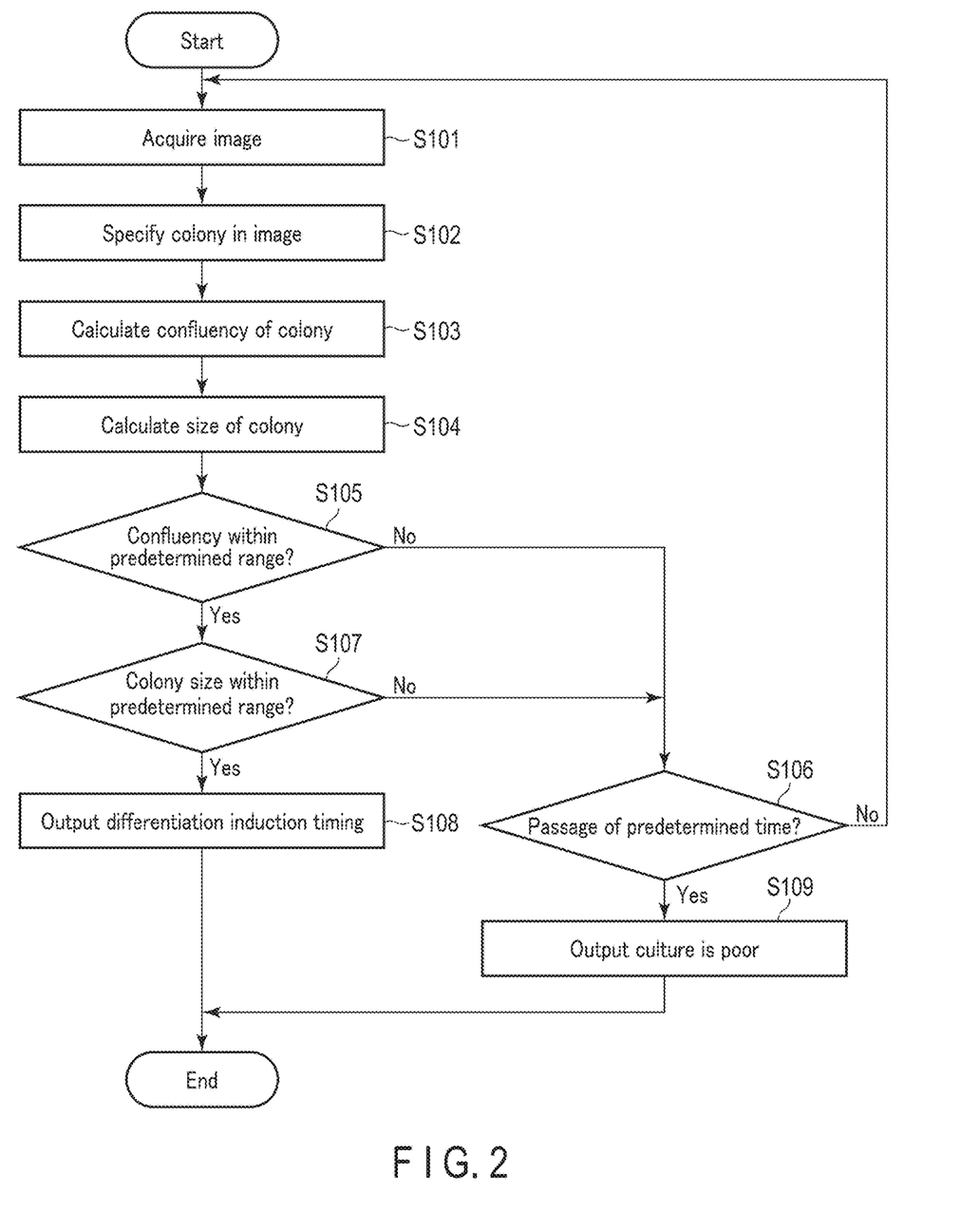
FIG. 2 is a flowchart for explaining an example of an operation of a cell analyzing device according to the first embodiment.

The operation of the cell analyzing device 200 will be explained with reference to the flowchart shown in FIG. 2, taking as an example a case where the cell analyzing device 200 that has acquired an image of a stem cell indicates the timing at which differentiation induction of the stem cell should be started.

In step S101, the image acquisition unit 212 of the cell analyzing device 200 acquires an observation image of stem cells in culture, such as iPS cells or ES cells, captured most recently, from, for example, the storage 130. In step S102, the colony specifying unit 214 of the cell analyzing device 200 specifies a colony of cells in the acquired image as the target. For example, the colony specifying unit 214 may extract a contour of a colony of cells in the image. In addition, the colony specifying unit 214 may sequentially specify whether each pixel in the image is inside or outside the cell colony. The colony specifying unit 214 may also specify the contour of each cell configuring the colony as necessary. The analysis target may be the entire region in the image or a partial range in the image.

In step S103, the confluency calculation unit 216 of the cell analyzing device 200 calculates the ratio of the cells present in the analysis target range, that is, the confluency of the colonies, based on the region of the specified colonies (cells) in the image. In step S104, the colony size calculation unit 220 of the cell analyzing device 200 calculates information on the size of the colony. For example, the size of the colony can be expressed by the area of the colony, the length of a major axis or a minor axis when the contour of the colony is elliptically approximated, or the like.

In step S105, the status determination unit 234 of the cell analyzing device 200 determines whether or not the confluency calculated in step S103 is within a predetermined range. Here, as the predetermined range, a confluency suitable for starting differentiation induction is set. When the confluency is not within the predetermined range, the processing proceeds to step S106.

In step S106, the status determination unit 234 of the cell analyzing device 200 acquires, for example, information on the elapsed time from the start of culture from the time measuring unit 232. The status determination unit 234 determines, for example, whether or not a predetermined time has elapsed from the start of culture. When the predetermined time has not elapsed, the processing returns to step S101. At this time, the cell analyzing device 200 waits until the image of cells are captured next, and when the image of cells are captured, in step S101, the image of the stem cells obtained by capturing is acquired. Thereafter, the processing of steps S102 to S105 are performed as described above.

When it is determined in step S105 that the confluency is within the predetermined range, the processing proceeds to step S107. In step S107, the status determination unit 234 of the cell analyzing device 200 determines whether or not the colony size acquired in step S104 is within a predetermined range. Here, as the predetermined range, a colony size suitable for starting differentiation induction is set. When the colony size is not within the predetermined range, the processing proceeds to step S106. That is, the above-described processing is repeated until the predetermined time elapses.

When it is determined in step S107 that the colony size is within the predetermined range, the processing proceeds to step S108. In step S108, the output data generation unit 242 of the cell analyzing device 200 generates information indicating that the timing is suitable for starting differentiation induction as output data, and the data output unit 244 outputs the output data. As a result, for example, the display 420 displays that the timing is suitable for starting differentiation induction. The processing of the cell analyzing device 200 is then ended.

When it is determined in step S106 that the predetermined time has elapsed, that is, when the confluency is within the predetermined range and the predetermined time has elapsed without determining that the colony size is within the predetermined range, the processing proceeds to step S109. Here, an example of measuring the elapsed time from the start of culture is described as an example; however, the present invention is not limited thereto. For example, an appropriate determination can be adopted depending on the purpose, such as an elapsed time after the medium is exchanged, an elapsed time after the passage operation is performed, or an elapsed time after a specific reagent is added.

In step S109, the output data generation unit 242 of the cell analyzing apparatus 200 generates information indicating that the culture state is poor as the output data, and the data output unit 244 outputs such output data. As a result, for example, the display 420 displays that the cell culture state is poor. The processing of the cell analyzing device 200 is then ended.

According to the present embodiment, when all of the confluency of the cell, the size of the colony, and the elapsed time are within an appropriate range as a timing at which differentiation induction should be started, for example, such matter is displayed on the display 420. On the other hand, when both the confluency of the cells and the size of the colonies do not fall within the appropriate range, and a predetermined time has elapsed, the fact that the culture is poor is displayed on, for example, the display 420. For example, it is possible to use only the confluency of colonies as a criterion for determination. However, even if the confluency is the same, it is not possible to distinguish between a case where there are many small colonies and a case where there are a few large colonies. Therefore, in the present embodiment, not only the confluency but also information on the size of the colony is used to determine the state of the cell. By using the confluency and the colony size for the determination, it is possible to perform the state determination with higher accuracy, for example, compared to a case where only one of the confluency or the colony size is used.

According to the present embodiment, the user can know whether or not to start the differentiation induction of the cultured stem cells by confirming the analysis result of the cell analyzing device 200. The user who has confirmed this result can perform an operation of, for example, peeling the cells in culture from the culture vessel, re-seeding the cells in the vessel for the differentiation step, and inducing differentiation. Based on the analysis result of such cell analyzing device 200, the success rate of the differentiation induction of the cells is improved.

Here, as the state of the cell to be determined, whether or not differentiation induction is possible is taken as an example; however, other states may be adopted as the state to be determined. The cell analyzing device 200 can specify the predetermined state by determining the state of the cell based on the confluency of the cell, the size of the colony, and the elapsed time as in the above-described embodiment.

The predetermined range used in step S105 and/or step S107 described above may be a range set by an input of the user, or may be a range set using the cell type or the elapsed time as a variable. These predetermined ranges may be, for example, values empirically obtained as confluencies or colony sizes suitable for starting differentiation induction, values logically derived from experiments, numerical calculations, or the like, or values obtained by other methods.

Second Embodiment

A second embodiment will be explained. Here, differences from the first embodiment will be explained, the same parts will be denoted by the same reference numerals, and explanations thereof will be omitted. In the present embodiment, a method of acquiring information on a colony size is different from that in the first embodiment.

Figure 3:
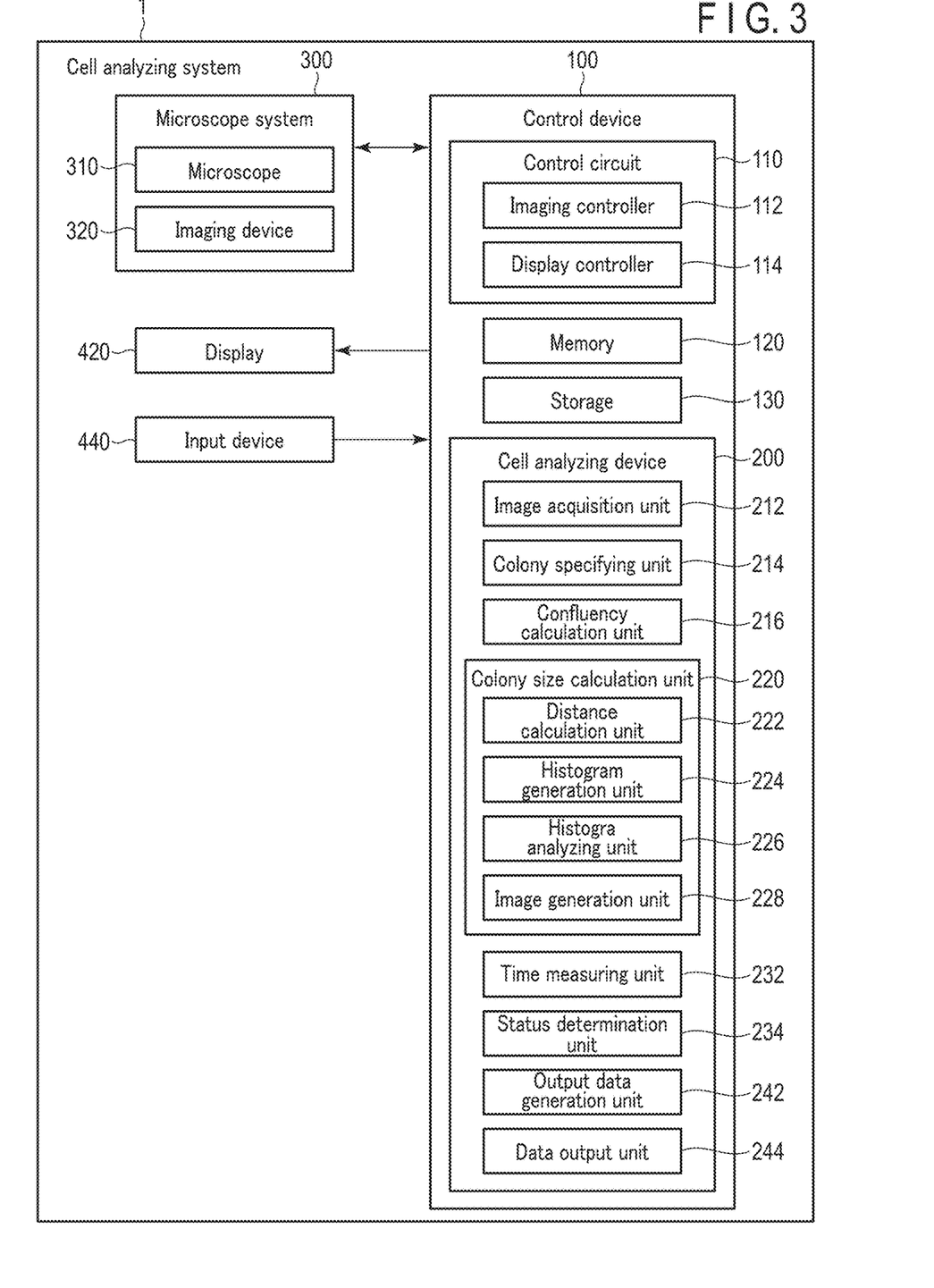
FIG. 3 is a block diagram schematically showing a configuration example of a cell analyzing system according to a second embodiment.

FIG. 3 schematically shows a configuration example of a cell analyzing system 1 according to the present embodiment. As shown in FIG. 3, the configuration of the cell analyzing system 1 including the control device 100, the microscope system 300, the display 420, the input device 440, and the like is the same as that of the first embodiment except for the internal configuration of the colony size calculation unit 220 of the cell analyzing device 200.

The colony size calculation unit 220 includes a distance calculation unit 222, a histogram generation unit 224, a histogram analyzing unit 226, and an image generation unit 228. The distance calculation unit 222 calculates the distance from each position in the image, particularly each position in the colony, to the nearest region outside the colony. That is, the distance calculation unit 222 calculates the distance from each position in the colony to the nearest region outside the colony. At each position outside the colony, the calculated distance value is 0. The histogram generation unit 224 generates a histogram of the distances calculated by the distance calculation unit 222. The histogram analyzing unit 226 calculates a feature amount of the histogram generated by the histogram generation unit 224. The feature amount is, for example, a maximum value of the distance or an absolute value of a gradient of the histogram described above. The image generation unit 228 generates an output image to be output from the cell analyzing device 200. The image generation unit 228 generates, for example, an image in which the distance to the nearest region outside the colony calculated by the distance calculation unit 222 is represented by color for each position, an image in which the image is superimposed on the image of the cultured cell, or the like.

Figure 4:
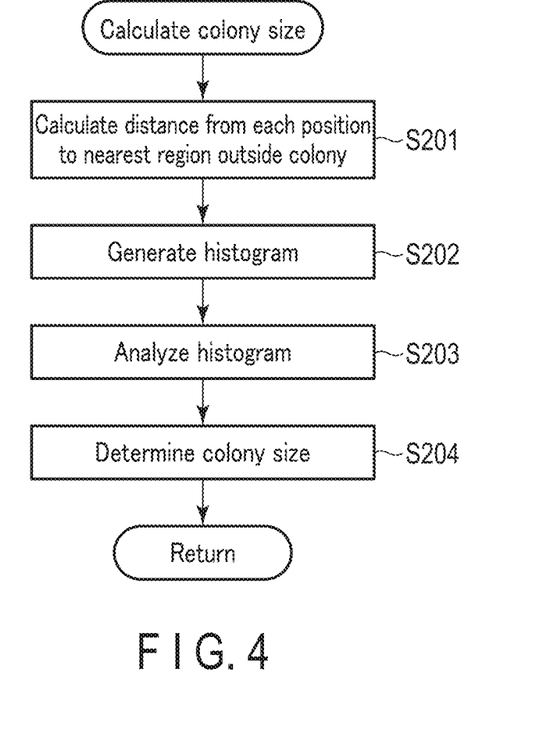
FIG. 4 is a flowchart for explaining an example of an operation related to calculation of a colony size according to the second embodiment.

The operation of the cell analyzing device 200 of the present embodiment will be explained. In the present embodiment, an operation as schematically shown in FIG. 4 is performed in the calculation of the colony size in step S104 of the operation of the first embodiment.

That is, in step S201, the distance calculation unit 222 of the colony size calculation unit 220 calculates the distance from each position in the image to be analyzed to the nearest region outside the colony. Here, each position in the image may be, for example, a position corresponding to each pixel of an observation image or a position of each cell. When the position of the cell is used, only the position where the cell exists is to be analyzed, and the position where the cell does not exist is not to be analyzed. Furthermore, each position may be targeted for the entire region in the image or may be targeted for a partial range in the image. The distance to the nearest region outside the colony for each position of interest may literally be the distance from the position of interest to the position of the nearest region outside the colony among the positions of the region outside the colony. A value equivalent to this distance may be set as the distance to the nearest region outside the colony. For example, as for the region inside the colony, the distance from the position of interest to the position of the closest contour or edge among the positions of the contour or edge of the colony may be set as the distance to the nearest region outside the colony. In the case where the distance to the contour or edge of the colony is set as the distance to the nearest region outside the colony, such distance is not calculated or set to 0 outside the colony.

In step S202, the histogram generation unit 224 of the colony size calculation unit 220 generates a histogram representing frequency distributions of the distances for the respective positions calculated in step S201. In step S203, the histogram analyzing unit 226 of the colony size calculation unit 220 performs necessary analysis on the histogram generated in step S202. The histogram analyzing unit 226 calculates a feature amount that is information related to the size of the colony as an analysis result.

In step S204, the colony size calculation unit 220 determines the colony size based on, for example, the histogram generated in step S202 and the feature amount calculated in step S203.

Note that the image generation unit 228 of the colony size calculation unit 220 may generate an output image together with the determination of the colony size. For example, the image generation unit 228 generates an image (heat map) in which the distance to the nearest region outside the colony calculated by the distance calculation unit 222 is represented by color for each position. The image generation unit 228 may use such an image as an output image, or may use an image obtained by superimposing such image on an image in which the original cultured cells are captured as an output image.

Figure 5:
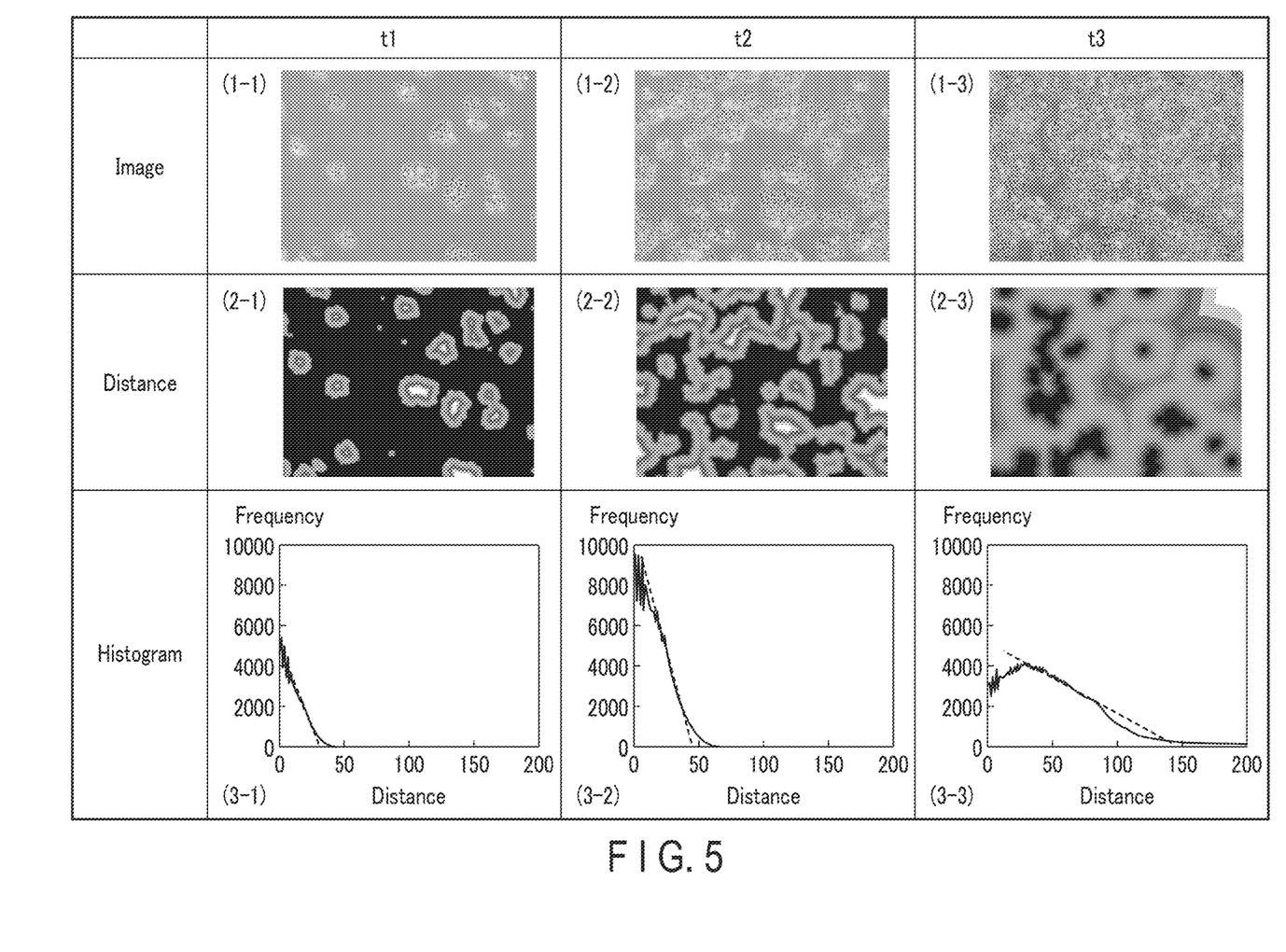
FIG. 5 is a diagram for explaining the calculation of the colony size of the cell analyzing device.

An example of data calculated by the colony size calculation unit 220 will be explained with reference to FIG. 5. In FIG. 5, images (1-1), (1-2), and (1-3) in the first row are examples of images of cells acquired by the image acquisition unit 212. Images (2-1), (2-2), and (2-3) in the second row are examples of images in which the distance to the nearest region outside the colony is represented by color. Here, black indicates a region in which the distance to the nearest region outside the colony is small. The region outside the colony is black because the distance from each position of the region outside the colony to the region outside the colony is 0. White indicates a region in which the distance to the nearest region outside the colony is large, and the center of the colony is white because the distance to the nearest region outside the colony is large. Graphs (3-1), (3-2), and (3-3) in the third row show examples of histograms representing the frequency of the distance to the nearest region outside the colony for each position. A broken line in the histogram is an approximate straight line for specifying the gradient of the histogram.

In FIG. 5, each column shows the result at each time of t1, t2, and t3. Time elapses in the order of t1 in the first column, t2 in the second column, and t3 in the third column. Therefore, when the images of the cells are viewed, the number of cells increases and the colonies become larger in the order of the image (1-1), the image (1-2), and the image (1-3). Here, as in the case of the image (2-1), the image (2-2), and the image (2-3), the distance to the nearest region outside the colony tends to increase as a whole as the colony becomes larger. On the other hand, the distance to the nearest region outside the colony is less likely to be affected by contact between adjacent colonies which may occur as the colonies grow larger.

Referring to the histograms (3-1), (3-2), and (3-3), as the number of cells increases, the maximum value of the distance naturally increases as described above. On the other hand, since the width of the distance distribution increases, the absolute value of the gradient of the histogram obtained using the approximate straight line indicated by the broken line decreases in the order of the histogram (3-1), the histogram (3-2), and the histogram (3-3). Furthermore, in the vicinity of the edge of the colony having a small distance value due to the contact between the adjacent colonies, a portion close to the contact portion enters the inside of the colony, and thus the distance value increases. Therefore, the absolute value of the gradient of the histogram also decreases by the contact between the colonies. As described above, the absolute value of the gradient of the histogram can be considered as a value representing the size of a colony, contact between colonies, and the like. In determining the timing to start differentiation induction, it is also important to distinguish between a case where there are a large number of small colonies and a case where there are a small number of large colonies. The gradient of the histogram is also effective for distinguishing between a case where there are a large number of small colonies and a case where there are a small number of large colonies.

Figure 6:
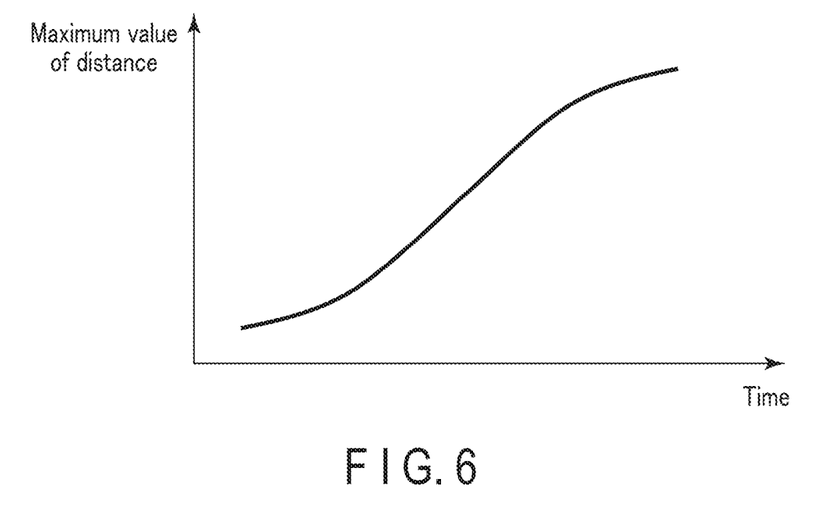
FIG. 6 is a diagram for explaining the calculation of the colony size of the cell analyzing device.
Figure 7:
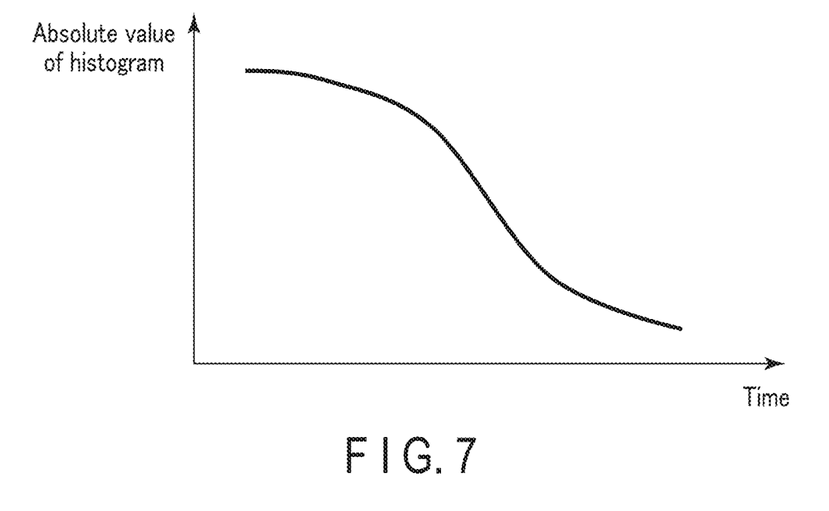
FIG. 7 is a diagram for explaining the calculation of the colony size of the cell analyzing device.

The analysis performed by the histogram analyzing unit 226 based on the histogram will be explained with reference to FIGS. 6 and 7. FIG. 6 shows the change in the maximum value of the distance from the nearest region outside the colony with the passage of culture time. The maximum value of the distance increases as the number of cells increases with the passage of culture time and the colony becomes larger. FIG. 7 shows the change in the absolute value of the gradient of the histogram with respect to the passage of culture time. As described above, the absolute value of the gradient of the histogram decreases as the number of cells increases with the passage of culture time, the size of the colony increases, and a position far from the edge of the colony appears. In addition, the absolute value of the gradient of the histogram also decreases due to contact between colonies. In the present embodiment, the histogram analyzing unit 226 calculates the maximum value of the distance, the absolute value of the gradient of the histogram, or the like as the feature amount.

Figure 8:
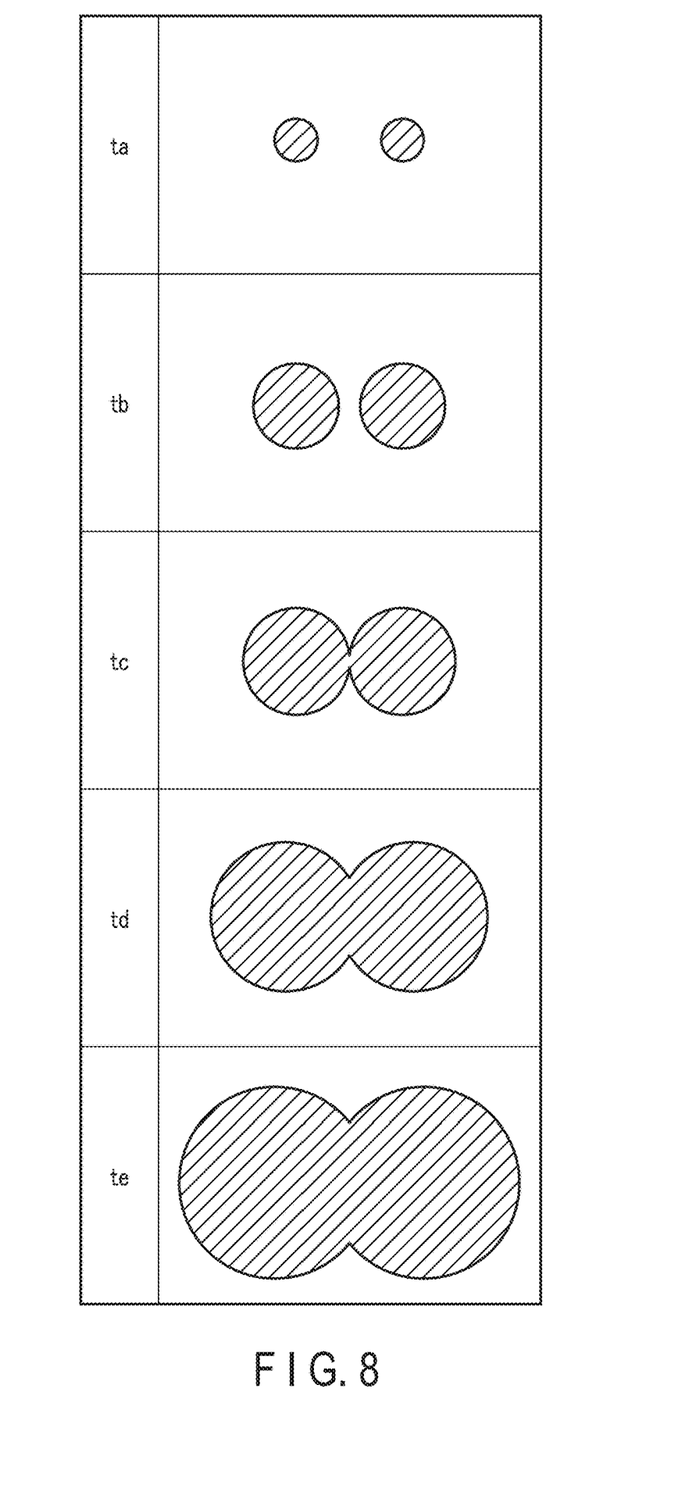
FIG. 8 is a diagram for explaining a comparative example.
Figure 9:
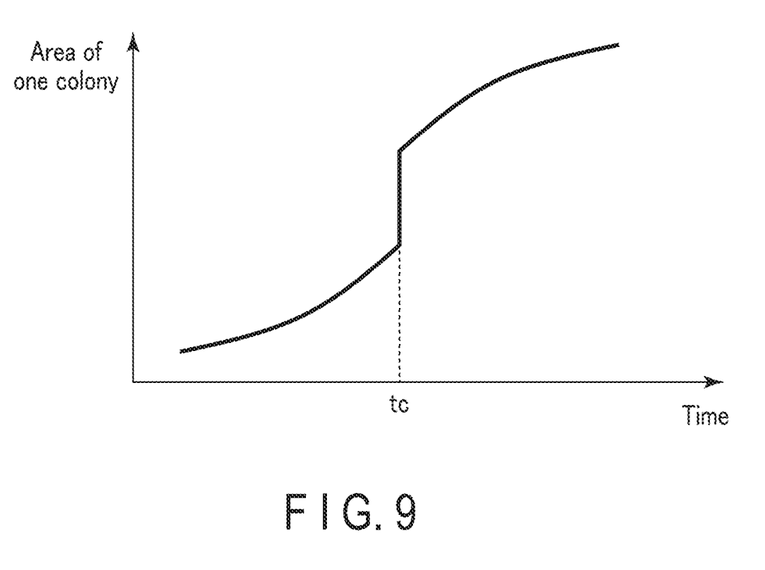
FIG. 9 is a diagram for explaining a comparative example.

As a comparative example, a case in which the size of one colony is used as a feature amount will be explained. FIG. 8 is a diagram for explaining the comparative example. Hatched circles and the like schematically show colonies. FIG. 8 schematically shows the change in colony size with the passage of time. It is assumed that two colonies become gradually larger with the passage of time ta, time tb, and time tc. Here, at time tc, the two colonies come into contact with each other and are recognized as one colony. Thereafter, it is assumed that the size of the colony increases with the passage of time td and time te. The change in size of one colony with the passage of culture time at this time will be considered. Here, the size of the colony can be expressed by the area of the colony, the length of the major axis or the minor axis when the contour of the colony is elliptically approximated, or the like. FIG. 9 shows the change in the area of one colony with the passage of the culture time. The length of the major axis when the contour of the colony is elliptically approximated shows the same tendency as the area of the colony.

As shown in FIG. 9, as the cells grow, the area of one colony gradually increases. As shown in FIG. 8, the two colonies come into contact with each other at time tc. At this time, the area of the colony recognized as one colony by the contact increases rapidly at time tc as shown in FIG. 9.

On the other hand, the maximum value of the distance and the values such as the gradient of the histogram obtained in the manner of the present embodiment are values that gradually change with an increase in the number of cells, and serve as indices that represent the size of the colony more appropriately. In addition, the maximum value of the distance and the values such as the gradient of the histogram serve as indices representing the colony size of the entire sample including not one colony but many colonies. Therefore, it is beneficial to determine the state of stem cells, such as whether differentiation induction can be started or not, using the colony size obtained in the present embodiment. The acquisition of the information representing the colony size according to the present embodiment is not limited to the analysis related to the start of differentiation induction, and can be used for specifying various cell states.

In the second embodiment, the maximum value of the distance to the nearest region outside the colony for each position is explained as the maximum value for the entire analysis range in which the histogram is generated. However, the present invention is not limited thereto, and the cell analyzing device 200 may set a selected predetermined colony as an analysis target, and set a maximum value of the distance in the selected colony as a feature amount. Similarly, the gradient of the histogram may be a gradient of a histogram generated by using a predetermined colony as an analysis target. Such an analysis result is useful as an index representing the size of a colony to be analyzed.

<Modification>

In the above-described first and second embodiments, an example in which the control device 100, the microscope system 300, the display 420, and the input device 440 configure the cell analyzing system 1 as a whole has been described; however, the present invention is not limited thereto. For example, the cell analyzing device 200 may be independent. That is, data of an image obtained by imaging with the microscope system can be stored in various storage media, a server on a network, or the like. The cell analyzing device 200 may acquire the stored image data, analyze the image data, and store output data as an analysis result in various storage media, a server on a network, or the like.

Additional advantages and modifications will readily occur to those skilled in the art. Therefore, the embodiment in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cell analyzing device comprising a control circuit configured to:
    acquire data of an observation image;
    determine an analysis target range within the observation image, the analysis target range including at least a part of an entire region of the observation image;
    specify a colony of a cultured cell in the observation image;
    specify a colony region in the observation image based on the specified colony;
    calculate an occupancy rate of the colony in the analysis target range, the occupancy rate of the colony in the analysis target range being a percentage of an overall area of the analysis target range occupied by the colony region;
    calculate a size of the colony; and
    determine a predetermined state of the colony based on (i) the occupancy rate of the colony in the analysis target range and (ii) the size of the colony;
    wherein the colony is a colony of a stem cell, and the predetermined state is a state suitable for starting differentiation induction for the colony.

2. The cell analyzing device according to claim 1, wherein the control circuit is configured to determine that the colony is in the predetermined state in a case in which each of (i) the occupancy rate of the colony in the analysis target range and (ii) the size of the colony is within a predetermined range.

3. The cell analyzing device according to claim 1, wherein the control circuit is configured to:
    specify the colony with respect to a region inside the colony and a region outside the colony;
    calculate a distance from each position in a region including the region inside the colony to a nearest region outside the colony; and
    calculate the size of the colony based on the distance.

4. The cell analyzing device according to claim 3, wherein the control circuit is configured to:
    generate a histogram of the distance for a predetermined range included in the observation image;
    calculate a feature amount of the histogram; and
    calculate the size of the colony based on the feature amount.

5. The cell analyzing device according to claim 4, wherein the feature amount is a gradient of the histogram or a maximum value of the distance.

6. The cell analyzing device according to claim 1, wherein the control circuit is configured to:
    measure a passage of time; and
    determine the state of the colony further based on (iii) the measured passage of time.

7. The cell analyzing device according to claim 6, wherein the control circuit is configured to determine that the colony is in the predetermined state in a case in which each of (i) the occupancy rate of the colony in the analysis target range, (ii) the size of the colony, and (iii) the passage of time is within a predetermined range.

8. A cell analyzing system comprising:
a microscope;
an imaging device configured to capture an image of a cultured cell obtained by the microscope to generate image data; and
the cell analyzing device according to claim 1,
wherein the control circuit acquires the image data generated by the imaging device as the data of the observation image.

9. The cell analyzing device according to claim 1, wherein the processor is configured to output information indicating a timing at which the differentiation induction should be started when it is determined that the colony is in the predetermined state.

* * * * *